United States Patent
De Vries et al.

(10) Patent No.: US 9,707,268 B2
(45) Date of Patent: Jul. 18, 2017

(54) ANGIOTENSIN TYPE 2 (AT2) RECEPTOR AGONISTS AND USES THEREOF

(71) Applicant: LANTHIOPEP B.V., Groningen (NL)

(72) Inventors: Louwe De Vries, Winsum (NL); Sieger Adriaan Nelemans, Leens (NL); Rick Rinck, Groningen (NL); Antonius Jacobus Marinus Roks, Dordrecht (NL); Gert Nikolaas Moll, Groningen (NL)

(73) Assignee: LANTHIOPEP B.V., Groningen (NL)

( * ) Notice: Subject to any disclaimer, the term of this patent is extended or adjusted under 35 U.S.C. 154(b) by 0 days.

(21) Appl. No.: 15/009,846

(22) Filed: Jan. 29, 2016

(65) Prior Publication Data

US 2016/0220632 A1    Aug. 4, 2016

Related U.S. Application Data

(62) Division of application No. 13/988,085, filed as application No. PCT/NL2011/050793 on Nov. 22, 2011, now Pat. No. 9,290,540.

(30) Foreign Application Priority Data

Nov. 23, 2010 (EP) .................................... 10192208

(51) Int. Cl.
| | | |
|---|---|---|
| A61K 38/12 | (2006.01) |
| C07K 7/06 | (2006.01) |
| A61P 43/00 | (2006.01) |
| C07K 7/64 | (2006.01) |
| A61K 45/06 | (2006.01) |

(52) U.S. Cl.
CPC .............. *A61K 38/12* (2013.01); *A61K 45/06* (2013.01); *C07K 7/06* (2013.01); *C07K 7/64* (2013.01)

(58) Field of Classification Search
CPC .... A61K 38/12; A61K 45/06; A61K 2300/00; C07K 7/06; C07K 7/64
See application file for complete search history.

(56) References Cited

U.S. PATENT DOCUMENTS

| | | |
|---|---|---|
| 5,091,390 A | 2/1992 | Ardecky |
| 5,166,206 A | 11/1992 | Allen |
| 5,177,074 A | 1/1993 | Allen |
| 5,240,928 A | 8/1993 | Allen |
| 5,250,521 A | 10/1993 | Allen |
| 5,252,574 A | 10/1993 | Allen |
| 5,260,285 A | 11/1993 | Allen |
| 5,312,820 A | 5/1994 | Ashton |
| 5,330,987 A | 7/1994 | Allen |
| 5,376,666 A | 12/1994 | Duncia |
| 5,412,097 A | 5/1995 | Chakravarty |
| 5,834,432 A | 11/1998 | Rodgers |
| 5,932,575 A | 8/1999 | Yanaka |
| 8,835,375 B2 | 9/2014 | Haas |
| 2009/0326026 A1 | 12/2009 | Alterman |

FOREIGN PATENT DOCUMENTS

| | | |
|---|---|---|
| CN | 1015733373 A | 11/2009 |
| EP | 0409332 | 1/1991 |
| EP | 0512675 | 11/1992 |
| WO | 9402142 | 2/1994 |
| WO | 9403435 | 2/1994 |
| WO | 9427597 | 12/1994 |
| WO | 9639164 | 12/1996 |
| WO | 9833813 | 8/1998 |
| WO | 98/58952 | 12/1998 |
| WO | 9926644 | 6/1999 |
| WO | 9939743 | 8/1999 |
| WO | 9940106 | 8/1999 |
| WO | 9940107 | 8/1999 |
| WO | 9942122 | 8/1999 |
| WO | 9943339 | 9/1999 |
| WO | 9945945 | 9/1999 |
| WO | 9946285 | 9/1999 |
| WO | 9952540 | 10/1999 |
| WO | 9958140 | 11/1999 |
| WO | 0002905 | 1/2000 |
| WO | 0009144 | 2/2000 |
| WO | 0038676 | 7/2000 |
| WO | 0056345 | 9/2000 |
| WO | 2004046128 | 6/2004 |
| WO | 2008130217 | 10/2008 |
| WO | 2009100513 | 8/2009 |

OTHER PUBLICATIONS

George et al, The renin-angiotensin system and cancer: old dog, new tricks, Nature Reviews, 2010, 10, pp. 745-759.*
Namsolleck et al, AT2 Receptor and Tissue Injury: Therapeutic Implications, Curr Hypertens Rep, 2014, 16, pp. 1-10.*
Nielsen, Angiotensin AT2 Receptor-Selective Agonists as Anti-Fibrotic Agents, from Monash University, available online on Jun. 2016, p. 1.*
Steckelings et al, AT2 receptor agonists: hypertension and beyond, Curr Opin Nephrol Hypertens, 2012, 21, pp. 142-146.*
Emma S. Jones, et al., AT2 receptors: Functional relevance in cardiovascular diseases, Pharmacology & Therapeutics 120 (2008), p. 292-316.
Leon D. Kluskens, et al., Angiotensin-(1-7) with Thioether Bridge: An Angiotensin-Converting Enzyme-Resistant, Potent Angiotensin-(1-7) Analog J. Pharmacol Exp Ther, 2009, 328, pp. 849-854.
Amit K. Galande, et al., Understanding Base-Assisted Desulfurization Using a Variety of Disulfide-Bridged Peptides, Biopolymers (Peptide Science) vol. 17, 534-551 (2003).
M. De Gaspearo, et al., International Union of Pharmacology, XXIII. The Angiotensin II Receptors, Pharmacological Reviews, vol. 52 No. 3, p. 415-472 (2000).
Ardaillou, Raymond, Angiotensin II Receptors, J. Am., Soc., Nephroi., 10, S30-39 (1999).

* cited by examiner

*Primary Examiner* — Julie Ha
*Assistant Examiner* — Li Ni Komatsu
(74) *Attorney, Agent, or Firm* — Licata & Tyrrell P.C.

(57) ABSTRACT

The invention relates to novel pharmaceutically-useful peptides, in particular cyclic peptides that are agonists of the AngII type 2 receptor (AT2 receptor). The invention further relates to the use of such peptides as medicaments, to pharmaceutical compositions containing them, and to their production.

18 Claims, 4 Drawing Sheets

ANGIOTENSIN TYPE 2 (AT2) RECEPTOR AGONISTS AND USES THEREOF

CROSS-REFERENCE TO RELATED APPLICATIONS

Figure 1:
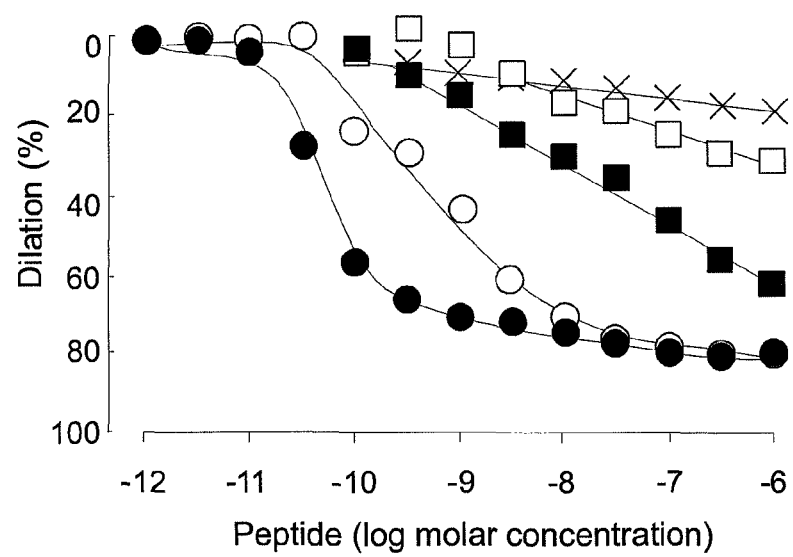

This application is a divisional of U.S. application Ser. No. 13/988,085 filed on Oct. 17, 2013, which is allowed, which is the US National Phase entry of PCT/NL2011/050793 filed on Nov. 22, 2011, each of which are incorporated by reference in their entireties.

The invention relates to novel pharmaceutically-useful peptides, in particular cyclic peptides that are agonists of the angiotensin II type 2 receptor (hereinafter the AT2 receptor). The invention further relates to the use of such peptides as medicaments, to pharmaceutical compositions containing them, and to synthetic routes to their production.

The endogenous hormone AngII is a linear octapeptide Asp-Arg-Val-Tyr-Ile-His-Pro-Phe) (SEQ ID NO:1), and is the active component of the renin-angiotensin system (RAS). It is produced by the sequential processing of the pro-hormone angiotensinogen by renin and angiotensin converting enzyme (ACE). The RAS plays an important role in the regulation of blood pressure, body fluid and electrolyte homeostasis. Ang II exerts these physiological actions in many organs including the kidneys, the adrenal glands, the heart, blood vessels, the brain, the gastrointestinal tract and the reproductive organs (de Gasparo et al, Pharmacol. Rev. (2000) 52, 415-472). Two main classes of AngII receptors have been identified, and designated as the type 1 receptor (hereinafter the ATI receptor) and the AT2 receptor. The ATI receptor is expressed in most organs, and is believed to be responsible for the majority of the biological effects of AngII. The AT2 receptor is more prevalent than the ATI receptor in fetal tissues, the adult ovaries, the adrenal medulla and the pancreas. An equal distribution is reported in the brain and uterus (Ardaillou, J. Am. Soc. Nephroi., 10, S30-39 (1999)). Several studies in adult individuals appear to demonstrate that, in the modulation of the response following AngII stimulation, activation of the AT2 receptor has opposing effects to those mediated by the ATI receptor.

The AT2 receptor has also been shown to be involved in apoptosis and inhibition of cell proliferation (see de Gasparo et al, supra). Further, it seems to play a role in blood pressure control. The functional relevance of AT2 receptors in cardiovascular disease is discussed in Jones et al. (Pharmacology & Therapeutics 120 (2008) 292-316). The expression of AT2 receptors has also been shown to increase during pathological circumstances, such as vascular injury, wound healing and heart failure (see de Gasparo et al, supra).

The expected pharmacological effects of agonism of the AT2 receptor are described generally in de Gasparo et al, supra. AT2 receptor agonists have been shown to be of potential utility in the treatment and/or prophylaxis of disorders of the alimentary tract, such as dyspepsia and irritable bowel syndrome, as well as multiple organ failure (see WO 99/43339).

AngII antagonists (which bind to the AT1 and/or AT2 receptors) have been disclosed in inter alia European patent applications EP 409 332, EP 512 675; international patent applications WO 94/27597, WO 94/02142, WO 95/23792 and WO 94/03435; and U.S. Pat. Nos. 5,091,390, 5,177,074, 5,412,097, 5,250,521, 5,260,285, 5,376,666, 5,252,574, 5,312,820, 5,330,987, 5,166,206, 5,932,575 and 5,240,928. US 2009/326026 discloses the use of tricyclic, imidazole-containing compounds as AT2 agonist. WO 2004046128 relates to bicyclic compounds which are useful as selective agonists of the AT2 receptor.

Peptide and non-peptide AT2 receptor agonists, unrelated structurally to those described herein, and potential uses thereof, have been disclosed in, for example, international patent applications WO 00/38676, WO 00/56345, WO 00/09144, WO 99/58140, WO 99/52540, WO 99/46285, WO 99/45945, WO 99/42122, WO 99/40107, WO 99/40106, WO 99/39743, WO 99/26644, WO 98/33813, WO 00/02905 and WO 99/46285; U.S. Pat. No. 5,834,432; and Japanese patent application JP 143695.

In view of the recent recognition of the AT2 receptor as an important new target for therapy, e.g. in the overall care of patients with hypertension, the present inventors set out to identify further effective and/or selective AT2 receptor agonists, which are expected to find utility in inter alia the above-mentioned conditions. It was surprisingly found that thioether-cyclized peptide analogs of Ang(1-7) extended with an additional amino acid at the N-terminus are potent agonists of the AT2 receptor.

Accordingly, there is provided a cyclic peptide compound consisting of the amino acid sequence Xaa$^1$-Asp-Arg-Ile/Val-Xaa$^5$-Ile/Val-His-Xaa$^8$ (SEQ ID NO:2) comprising a thioether-bridge linkage between the side chains of Xaa5 and Xaa8 such that amino acids Xaa5 and Xaa8 together form a structure according to either one of the general formula:

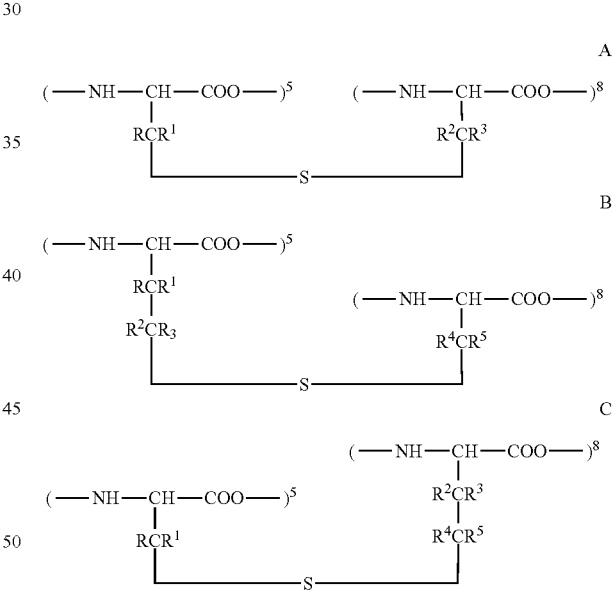

wherein R, R$^1$, R$^2$, R$^3$, R$^4$ and R$^5$ are independently selected from —H, a lower (e.g. C$_1$-C$_{10}$) alkyl or aralkyl group, and wherein Xaa$^1$ is selected from the group consisting of charged amino acids, aromatic amino acids and hydrophobic amino acids, and protease-resistant variants thereof, or a pharmaceutically acceptable salt thereof.

Peptide compounds and salts are referred to together hereinafter as "the compounds of the invention".

Pharmaceutically-acceptable salts include acid addition salts and base addition salts. Examples of such salts are acid addition salts formed with inorganic acids, for example, hydrochloric acid, hydrobromic acid, sulfuric acid, phosphoric acid, nitric acid, and the like. Salts may also be formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, and the like. Salts may be formed with polyvalent metal cations such as zinc, calcium, bismuth, barium, magnesium, aluminum, copper, cobalt, nickel and the like or with an organic cation formed from N,N'-dibenzylethylenediamine or ethylenediamine, or combinations thereof (e.g., a zinc tannate salt). The non-toxic, physiologically acceptable salts are preferred. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo or by freeze-drying). Salts may also be prepared by exchanging a counter-ion of a compound of the invention in the form of a salt with another counter-ion, for example using a suitable ion exchange resin.

Preferably, R, $R^1$, $R^2$, $R^3$, $R^4$ and $R^5$ are independently selected from H and $CH_3$.

It was found that AT2 receptor interaction requires the presence of a lanthionine ring linking the amino acids at positions 5 and 8 in the above formula. Furthermore, the N-terminal extension should be limited to a single amino acid residue as it was found that the addition of a second additional residue abolished AT2 receptor interaction.

In one embodiment, the invention provides a peptide comprising a thio-ether bridge according to formula A, i.e. wherein the linkage between the amino acids at positions 5 and 8 has the meaning —$RCR^1$—S—$R^2CR^3$—, wherein R, $R^1$, $R^2$ and $R^3$ are independently selected from —H, a lower (e.g. $C_1$-$C_{10}$) alkyl or aralkyl group. R, $R^1$, $R^2$ and $R^3$ are preferably independently selected from H and $CH_3$. Peptides comprising a thio-ether bridge according to formula A can be made for example by lantibiotic enzymes or by sulfur extrusion of a disulfide. The disulfide from which the sulfur is extruded can be formed by a D-cysteine in position 5 and a L-cysteine in position 8 or by one D-cysteine in position 5 and a L-penicillamine in position 8 [Galande, Trent and Spatola 2003 Biopolymers 71, 534-551].

Alternatively, the linkage of the two amino acids can be composed of $RCR^1$-$R^2CR^3$—S—$R^4CR^5$ (Formula B) or $RCR^1$—S—$R^4CR^5$—$R^2CR^3$ (Formula C), in which R, $R^1$, $R^2$, $R^3$, $R^4$ and $R^5$ independently represent —H, a lower (e.g. $C_1$-$C_{10}$) alkyl or aralkyl group. Peptides comprising a thio-ether bridge according to formula B can for instance be made by sulfur extrusion of a disulfide formed by a D-homocysteine in position 5 and a L-cysteine in position 8 [Galande, Trent and Spatola 2003 Biopolymers 71, 534-551]. Likewise, peptides comprising a thio-ether bridge according to formula C can for instance be made by sulfur extrusion of a disulfide formed by a D-cysteine in position 5 and a L-homocysteine in position 8 [Galande, Trent and Spatola 2003 Biopolymers 71, 534-551].

It is convenient that a peptide analog of the invention can be made in a biological system, in particular making use of the lantibiotic enzyme system of a (bacterial) host cell. Accordingly, peptides comprising a thio-ether bridge according to formula A are preferred.

In one aspect, $Xaa^1$ is a positively charged amino acid, preferably Lys or Arg or peptidase-resistant variant or derivate thereof. In another aspect, $Xaa^1$ is a negatively charged amino acid, preferably Asp or Glu or peptidase-resistant variant or derivate thereof. Alternatively $Xaa^1$ is a hydrophobic amino acid, preferably Ile, Leu or Val, or an aromatic amino acid, preferably Tyr or Phe, or peptidase-resistant variant or derivative thereof. Peptidase-resistant variants and derivatives can protect the analog against degradation by amino peptidase(s). In one embodiment, $Xaa^1$ is a peptidase-resistant amino acid variant or derivate, for example one of the above mentioned amino acids in the D-configuration. Other suitable derivatives include those in which the free amino group is cyclized to form a ring structure, like pyroglutamate (pGlu) wherein the terminus is a lactam ring.

The residues at positions 2, 3, 4, 6, and 7 can be varied as long as biological activity is maintained. In a preferred embodiment, Xaa2 is Asp, Xaa3 is Arg, Xaa4 is Val, Xaa6 is Ile and/or Xaa 7 is His. The stereochemistry of the residues involved in the thioether bridge can be either the L- or D-form. Cyclic peptides wherein Xaa5 is a D-stereoisomer and/or Xaa8 is an L-stereoisomer are preferred. Most preferred is an analog wherein $Xaa^5$ is a D-stereoisomer and $Xaa^8$ is an L-stereoisomer.

Thioether-cyclized analogs of Angiotensin-(1-7) are known in the art. See for example Kluskens et al. (J Pharmacol Exp Ther. 2009 March; 328(3):849-54) and WO2008/130217. Linear angiotensin analogs with or without N-terminal extensions of 1 to 3 amino acids have been described by K. Rodgers et al., for example in WO99/40106, WO99/52540 and WO96/39164. However, a cAng(1-7) analog having an N-terminal extension with a single residue selected from the charged amino acids, aromatic amino acids and hydrophobic amino acids has not been taught or suggested in the art.

According to specific embodiments of the invention, the cyclic peptide compound is selected from the group consisting of:

```
                                        (SEQ ID NO: 3)
Lys-Asp-Arg-Val-Abu/Ala-Ile-His-Abu/Ala
(abbreviated to "K-cAng(1-7)")

(SEQ ID NO: 4)
Asp-Asp-Arg-Val-Abu/Ala-Ile-His-Abu/Ala
(abbreviated to "D-cAng(1-7)")

(SEQ ID NO: 5)
Tyr-Asp-Arg-Val-Abu/Ala-Ile-His-Abu/Ala
(abbreviated to "Y-cAng(1-7)")

(SEQ ID NO: 6)
Ile-Asp-Arg-Val-Abu/Ala-Ile-His-Abu/Ala
(abbreviated to "I-cAng(1-7)")

(SEQ ID NO: 7)
Asn-Asp-Arg-Val-Abu/Ala-Ile-His-Abu/Ala
(abbreviated to "N-cAng(1-7)")
``` under the provision that the peptide does not contain two Abu (2-aminobutyric acid) residues. In view of their potency as potent vasodilating peptides, compounds K-cAng(1-7) and Y-cAng(1-7) are particularly preferred.

Compounds of the invention are useful because they possess pharmacological activity. The compounds of the invention are therefore indicated as pharmaceuticals. In particular, compounds of the invention are agonists of the AT2 receptor, and, especially, are selective agonists of that sub-receptor, for example as demonstrated in the tests described below. The compounds of the invention are expected to be useful in those conditions where AT2 receptors are expressed and their stimulation is desired or required.

The compounds of the invention are further indicated in the treatment of conditions characterised by vasoconstriction, increased cell growth and/or differentiation, increased cardiac contractility, increased cardiovascular hypertrophy, and/or increased fluid and electrolyte retention. Furthermore, the compounds of the invention are indicated in the treatment of stress-related disorders, and/or in the improvement of microcirculation and/or mucosa-protective mechanisms. Accordingly, compounds of the invention are expected to be useful in the treatment of disorders, which may be characterised as indicated above, and which are of, for example, the gastrointestinal tract, the cardiovascular system, the respiratory tract, the kidneys, the eyes, the female reproductive (ovulation) system and the central nervous system (CNS). Also provided is a method for accelerating tissue repair, comprising administering to a subject in need thereof a therapeutically effective dose of a peptide compound of the invention.

Disorders of the gastrointestinal tract that may be mentioned include oesophagitis, Barrett's oesophagus, gastric ulcers, duodenal ulcers, dyspepsia (including non-ulcer dyspepsia), gastro-oesophageal reflux, irritable bowel syndrome (IBS), inflammatory bowel disease (IBD), pancreatitis, hepatic disorders (such as hepatitis), gall bladder disease, multiple organ failure (MOF) and sepsis. Other gastrointestinal disorders that may be mentioned include xerostomia, gastritis, gastroparesis, hyperacidity, disorders of the biliary tract, coelicia, Crohn's disease, ulcerative colitis, diarrhoea, constipation, colic, dysphagia, vomiting, nausea, indigestion and Sjögren's syndrome. Disorders of the respiratory tract that may be mentioned include inflammatory disorders, such as asthma, obstructive lung diseases (such as chronic obstructive lung disease), pneumonitis, pulmonary hypertension and acute respiratory distress syndrome. Disorders of the kidneys that may be mentioned include renal failure, nephritis and renal hypertension. Disorders of the eyes that may be mentioned include diabetic retinopathy, premature retinopathy and retinal microvascularisation. Disorders of the female reproductive system that may be mentioned include ovulatory dysfunction. Cardiovascular disorders that may be mentioned include hypertension, cardiac hypertrophy, cardiac failure, artherosclerosis, arterial thrombosis, venous thrombosis, endothelial dysfunction, endothelial lesions, post-balloon dilatation stenosis, angiogenesis, diabetic complications, microvascular dysfunction, angina, cardiac arrhythmias, claudicatio intermittens, preeclampsia, myocardial infarction, reinfarction, ischaemic lesions, erectile dysfunction and neointima proliferation. Disorders of the CNS that may be mentioned include cognitive dysfunctions, dysfunctions of food intake (hunger/satiety) and thirst, stroke, cerebral bleeding, cerebral embolus and cerebral infarction. Peptide compounds of the invention are also of use for augmenting erythropoiesis, e.g. by contacting erythroid progenitor cells with at least one peptide compound in an amount effective to augment erythropoiesis.

Compounds of the invention may also be useful in the modulation of growth metabolism and proliferation, for example in the treatment of hypertrophic disorders, prostate hyperplasia, autoimmune disorders, psoriasis, obesity, neuronal regeneration, the healing of ulcers, inhibition of adipose tissue hyperplasia, stem cell differentiation and proliferation, cancer (e.g. in the gastrointestinal tract, lung cancer, etc), apoptosis, tumours (generally) and hypertrophy, diabetes, neuronal lesions and organ rejection.

The compounds of the invention are indicated both in the therapeutic and/or prophylactic treatment of the above conditions.

According to a further aspect of the invention there is thus provided the compounds of the invention for use as pharmaceuticals. Also provided is a pharmaceutical composition comprising at least one peptide compound of the invention and a pharmaceutically acceptable carrier and/or adjuvant. The pharmaceutical compositions contain the compounds according to the invention in admixture with organic or inorganic carriers suitable for enteral or parenteral administration. Thus pharmaceutical compositions may be formulated as solid lyophilizates, in which various inert compounds not reacting with peptides, e.g., hydrocarbons can be used as carriers. When the pharmaceutical compositions are formulated as dilute or concentrated suspensions or emulsions, they contain also various preserving agents and stabilizing agents. Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

According to a further aspect of the present invention, there is provided a method of treatment of a condition in which endogenous production of AT2 receptor agonists is deficient, and/or a condition where an increase in the effect of AT2 receptor agonists is desired or required, and/or a condition where AT2 receptors are expressed and their stimulation is desired or required, which method comprises administration of a therapeutically effective amount of a compound of the invention to a person suffering from, or susceptible to, such a condition.

The compounds of the invention will normally be administered orally, intravenously, subcutaneously, buccally, rectally, dermally, nasally, tracheally, bronchially, by any other parenteral route or via inhalation, in a pharmaceutically acceptable dosage form.

When the condition to be treated is multiple organ failure, preferred routes of administration are parenteral (e.g. by injection). Otherwise, the preferred route of administration for compounds of the invention is oral. The compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like.

Such formulations may be prepared in accordance with standard and/or accepted pharmaceutical practice.

According to a further aspect of the invention there is thus provided a pharmaceutical formulation including a compound of the invention, in admixture with a pharmaceutically acceptable adjuvant, diluent or carrier.

Compounds of the invention may also be administered in combination with other AT2 agonists that are known in the art, as well as in combination with AT1 receptor antagonists that are known in the art, such as losartan, or in combination with an inhibitor of angiotensin converting enzyme (ACE), or in combination with Mas receptor agonists e.g. 4,7 cyclic angiotensin-(1-7) or angiotensin converting enzyme2 (ACE2).

In a specific aspect, the invention relates to use of compounds of the invention in accelerating the growth or healing of tissue. For example, provided is a peptide compound according to the invention for use in tissue repair. Also provided is a composition for accelerating wound healing, comprising a suitable carrier or diluent and an amount effective to accelerate wound healing of at least one peptide compound of the invention. The compound can be administered in a matrical or micellar solution. In one embodiment, the compound is administered at a rate of at least 0.1 ng per kg body weight in a suitable carrier or diluent. The carrier or diluent may be selected from the group consisting of carboxymethyl cellulose preparations, crystalloid preparations, viscoelastics, polyethylene glycols and polypropylene glycols.

The compound can advantageously be administered in conjunction with a wound dressing.

According to a further aspect of the invention, there is provided a combination product comprising (A) a peptide compound of the invention; and (B) selected from an AT1 receptor antagonist or an ACE inhibitor, and/or (C) a Mas receptor agonist, or ACE2, wherein each of components (A), (B) and/or (C) is formulated in admixture with a pharmaceutically-acceptable adjuvant, diluent or carrier. Such combination products provide for the administration of compound of the invention in conjunction with an AT1 receptor antagonist, or an ACE inhibitor, a Mas receptor agonist, or ACE2 and may thus be presented either as separate formulations, wherein at least one of those formulations comprises compound of the invention, and at least one comprises for instance AT1 receptor antagonist, or ACE inhibitor, or may be presented (i.e. formulated) as a combined preparation (i.e. presented as a single formulation including compound of the invention and AT1 receptor antagonist or ACE inhibitor).

Thus, there is further provided: (1) a pharmaceutical formulation including a compound of the invention and an AT1 receptor antagonist, or an ACE inhibitor or a Mas receptor agonist, or ACE2, in admixture with a pharmaceutically-acceptable adjuvant, diluent or carrier; and (2) a kit of parts comprising components:

(a) a pharmaceutical formulation including a compound of the invention, in admixture with a pharmaceutically-acceptable adjuvant, diluent or carrier; and (b) a pharmaceutical formulation including an AT1 receptor antagonist, or an ACE inhibitor, (c) a Mas receptor agonist, or ACE2 in admixture with a pharmaceutically acceptable adjuvant, diluent or carrier, which components (a), (b) and (c) are each provided in a form that is suitable for administration in conjunction with the other.

Depending upon the disorder and patient to be treated and the route of administration, the compounds of the invention may be administered at varying doses.

Although doses will vary from patient to patient, suitable doses e.g. for subcutaneous administration are in the range of about 1-1000 microgram/kg/day per patient, administered in single doses. More preferred daily doses are in the range 40 to 80 microgram/kg/day per patient. Intravenous doses are identical to subcutaneous doses. Pulmonary doses are about 4-fold higher than subcutaneous doses. Oral doses are at least five fold higher than subcutaneous doses and strongly depend on the applied formulation. Compounds of the invention can also be administered once per week. Weekly doses are about 10- to 30-fold higher than daily doses.

In any event, the physician, or the skilled person, will be able to determine the actual dosage which will be most suitable for an individual patient, which is likely to vary with the condition that is to be treated, as well as the age, weight, sex and response of the particular patient to be treated. The above-mentioned dosages are exemplary of the average case; there can, of course, be individual instances where higher or lower dosage ranges are merited, and such are within the scope of this invention. Compounds of the invention have the advantage that they bind selectively to, and exhibit agonist activity at, the AT2 receptor. By compounds which "bind selectively" to the AT2 receptor, we include that the affinity ratio for the relevant compound (AT2:AT1) is at least 5:1, preferably at least 10:1 and more preferably at least 20:1. The compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art.

LEGEND TO THE FIGURES

FIG. 1. KcAng-(1-7) and YcAng-(1-7) are highly potent vasodilators.

KcAng-(1-7) and YcAng-(1-7) induce vasodilation of phenylephridine-precontracted rings of aorta of Sprague Dawley rat. x: control; □: native angiotensin-(1-7); ■: cAng-(1-7); ○: KcAng-(1-7); ●: YcAng-(1-7).

Figure 2:
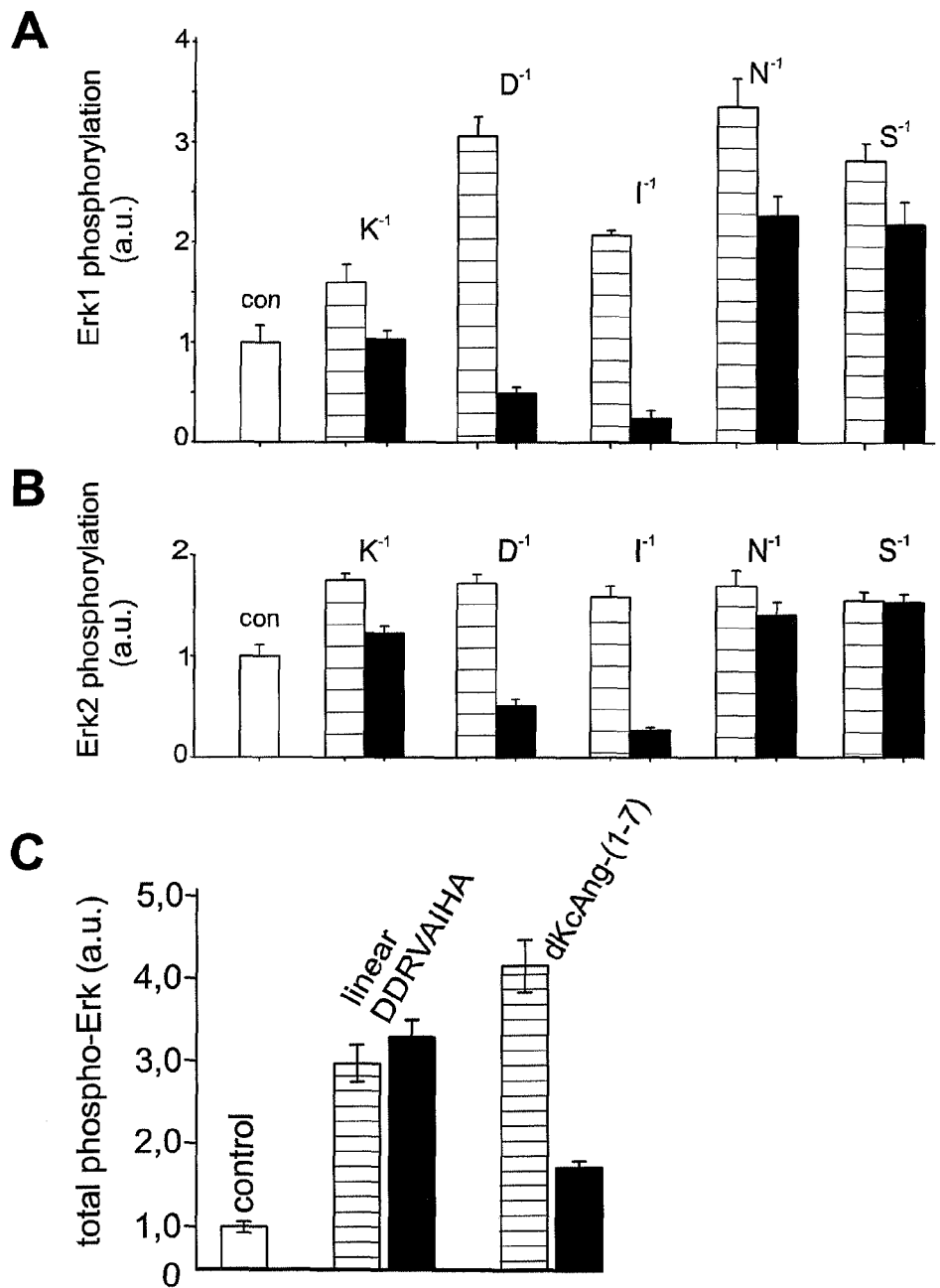

FIG. 2. N-extended cAng-(1-7) analogs require the 4,7 thioether ring for agonistic action via the AT2 receptor. cAng-(1-7) is a 4,7 thioether bridged Ang-(1-7). XcAng-(1-7), which is cAng-(1-7) with one variable additional amino acid at position-I (i.e. the residue denoted as Xaa1 herein above), induce Erk1 (FIG. 2A) and Erk2 (FIG. 2B) and total Erk phosphorylation (FIG. 2C). Open bars: controls; hatched bars: peptide induced Erk phosphorylation; black bars: peptide-induced Erk phosphorylation after pretreatment with the AT2 receptor antagonist PD 123319. At the bars (FIGS. 2A and 2B) the identity of the amino acid "X" at position −1 of XcAng-(1-7) is indicated. Pretreatment with PD123319 did not affect the ScAng-(1-7)-induced Erk2 phosphorylation (FIG. 2B), nor the linear-DDRVAIHA (SEQ ID NO:4)-induced total Erk phosphorylation (FIG. 2C). dKcAng-(1-7) is cAng-(1-7) with an N-terminal extension with a D-isomer of Lys.

Figure 3:
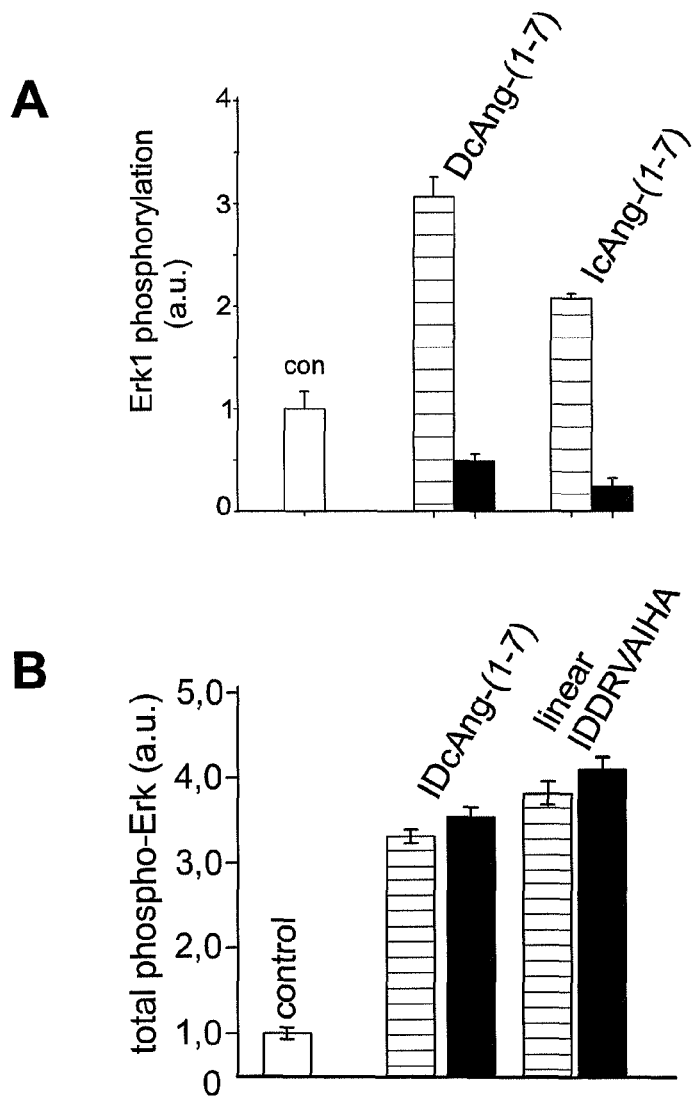

FIG. 3. AT2 receptor stimulation is not exerted by cAng-(1-7) analogs with two amino acids N-terminal extension. Panel A: DcAng-(1-7) and IcAng-(1-7) induced Erk1 phosphorylation of Erk1 in HBE cells. Panel B: IDcAng-(1-7) and IDDRVAIHA (SEQ ID NO:8)-induced total Erk phosphorylation in HBE cells. Open bar: control; hatched bars: peptide-induced ERKphosphorylation without pretreatment of the HBE cells; black bars: peptide-induced ERK phosphorylation after a pretreatment with PD123319.

Figure 4:
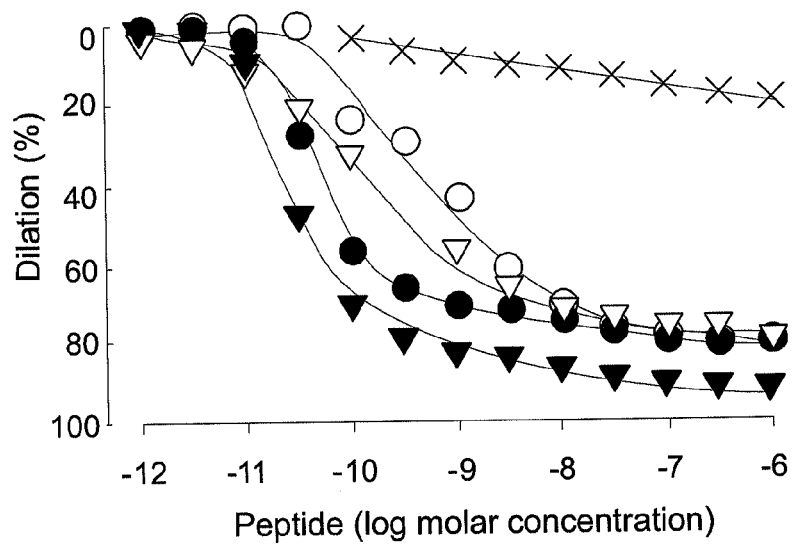

FIG. 4. N-extended cAng-(1-7) analogs do not act via the Mas receptor.

The Mas receptor antagonist D-Pro7 does not inhibit the KcAng-(1-7)- and YcAng-(1-7)-induced vasodilation of phenylephridine-precontracted rings of aorta of Sprague Dawley rat. x: control; ○: KcAng-(1-7); ∇: KcAng-(1-7)

and Mas receptor antagonist D-Pro7; ●: YcAng-(1-7); ▼: YcAng-(1-7) and Mas receptor antagonist D-Pro7.

EXAMPLES

Example 1. KcAng-(1-7) and YcAng-(1-7) are Potent Vasodilators

This example demonstrates that N-extended cAng-(1-7) analogs can strongly induce vasodilation in precontracted aorta rings from Sprague Dawley rats.

Materials and Methods.

Peptides: KDRVdCIHC, and YDRVdCIHC wherein dC stands for D-cysteine were purchased from JPT. Specified pathogen-free male Sprague Dawley rats (SD) (Harlan, Zeist, The Netherlands), weighing 350-450 gram were used. Prior to the experiment, the animals were housed together with free access of tap water and solid chow (Harlan, Zeist, The Netherlands) in a temperature and humidity controlled room and a 12112h light/dark cycle. All protocols described were approved by the University of Groningen Committee for Animal Experimentation.

Thioether-bridged peptides were obtained from the disulfide bridged peptide via base-assisted sulfur extrusion as previously (Galande A K, et al 2003. Biopolymers 71:534-551).

Vasodilation on precontracted aorta-rings. Arterial rings for organ bath experiments were prepared as described previously (Kluskens L D, et al. 2009. J Pharmacol Exp Ther 328:849-54). Before testing the vasodilating effects of the peptides the rings were precontracted to 50% of their maximum contraction level with 30 nM phenylephrine (PE). The 5,8 thioether bridged peptides KDRV[AIHA]C (SEQ ID NO:3) or YDRV[AIHA]c (SEQ ID NO:5) were added cumulatively in a range of 0.1 nM to 1 µM. Vasodilation data are represented as percentage of relaxation of 30 nM PE contraction.

Results.

FIG. 1 demonstrates the capacity of KcAng-(1-7) and YcAng-(1-7) to induce vasodilation of precontracted aorta rings from Sprague Dawly rats. Both peptides had already at sub-nM concentration significant vasodilating capacity.

Conclusion.

These data demonstrate that KcAng-(1-7) and YcAng-(1-7) are highly potent vasodilating peptides.

Example 2. N-Extended cAng-(1-7) Analogs Require the 4,7 Thioether Ring for Agonistic Action Via the AT2 Receptor Introduction.

This example shows the capacity of thioether-bridged cAng-(1-7), if extended with one N-terminal amino acid, to stimulate extracellular-signal-regulated kinase (ERK) phosphorylation in human bronchial epithelial (HBE) cells. The AT2 receptor specificity of the above thioether bridged peptides is established by measuring whether or not the peptide-induced ERK phosphorylation could be inhibited by PD123319, a well known antagonist of the AT2 receptor. In addition it is demonstrated that the thioether ring in the N-terminally extended analogs is required for the agonistic action via the AT2 receptor.

Materials and Methods.

Peptides were purchased from JPT: linear DDRVAIHA (SEQ ID NO:4), dKDRVdCIHC KDRVdCIHC, DDRVdCIHC, IDRVdCIHC, NDRVdCIHC, SDRVdCIHC, in which dK stands for D-lysine and dC stands for D-cysteine. The AT2 receptor antagonist PD 123319 was from Axon Medchem. Studies were performed using the immortal human bronchial epithelial cell line HBE (Cozens A L, et al. 1994 CFTR expression and chloride secretion in polarized immortal human bronchial epithelial cells. Am J Respir Cell Mol Biol 10:38-47). All culture media and supplements, multi-well plates and flasks were from PAA.

Cell culture. Multi-well plates received 1 ml from a coating solution (for 112 ml: F12 medium 100 ml; bovine serum albumin 10 ml (1 mg/ml); collagen I, Bovine 1 ml (3 mg/ml); human fibronectin 1 ml (1 mg/ml)) and were incubated for 6 hours at 37° C. and 5% $CO_2$. Subsequently the coating solution was discarded and the plates were dried for 2 hours in the laminar flow cabinet. In each 12 well plate $8.10^4$ HBE cells were seeded per well followed by incubation for 24 hours at 37° C. and 5% $CO_2$. Cell culture medium was prepared by adding 432.2 ml MEM 199 basic medium to 50 ml (15%) FCS and 5 ml L-Glutamin (200 mM), 10 ml Penicillin/Streptomycin (10.000 units/ml/10 mg/ml) and 2.8 ml Gentamycin (10 mg/ml). At 85-90% confluency medium was replaced by medium without FCS and growth factors followed by again 24 hours incubation at 37° C. and 5% $CO_2$.

Erk1 and Erk2 phosphorylation. The medium was removed from each well and was washed once with HBS buffer without calcium and magnesium. The capacity of peptide at $10^{-6}$ M was tested after 20 min preincubation with either $10^{-6}$ M of PD123319 or concomitant controls, followed by washing Challenges and concomitant controls were performed at 1 ml/well during 10 min. All samples were tested in triplicate. After the challenge 150 µl RIPA buffer (RIPA, TBS, 1% Nonidet P-40, 0.5% sodium deoxycholate, 0.1% SDS, 0.004% sodium azide, 1% PMSF (2 mM final concentration), 1% sodium orthovanadate (1 mM final concentration) and 1% protease inhibitor cocktail) was added to each well. The plates were incubated for 15 minutes at 4° C. The lysed cells were scraped from the surface. The lysate was transferred to 1.5 ml eppendorf cups and centrifuged 5 minutes at 12.700×g to pellet the cell debris. The supernatant was transferred into new cups and of a 5 µl sample the total protein content was determined via the DC protein assay according to lowry (Bio-Rad), with BSA used as calibration protein. Protein was separated on gel and blotted with p-ERK mouse monoclonal IgG2a and mouse GAPDH anti-rat IgG1 antibodies and as a second antibody goat anti-mouse IgG-AP. The phosphorylated Erk proteins and GAPDH were stained with BCIP/NBT and quantified relative to GAPDH and total Erk using TotalLab software. Alternatively, total Erk phosphorylation was measured after permeabilization of the non-detached cells.

Results.

FIG. 2AB shows that cAng-(1-7) analogs which are extended with one amino acid at the N-terminus stimulate ERK.I and to a lesser extent ERK2 phosphorylation. ERK.I and ERK.2 phosphorylation could be inhibited by the AT2 antagonist PD123319. The extent by which the AT2 antagonist PD 123319 could inhibit the peptide-induced ERK phosphorylation was dependent on the amino acid at the N-terminally extended position "−1". Inhibition of ERK phosphorylation by PD123319 was complete in the cases of Asp, Lys and He at the extended position. When Asn or Ser were present at the extended position the inhibition of ERK.I phosphorylation was less and inhibition of ERK2 phosphorylation was also less or absent. FIG. 2C demonstrates that the linear peptide DDRVAIHA (SEQ ID NO:4) induced Erk phosphorylation, but for this linear peptide the induced Erk phosphorylation could not be inhibited by PD123319. On the other hand, Erk phosphorylation induced by the thioether bridged dKcAng-(1-7) could be inhibited by PD123319.

Conclusions.

These data clearly prove that cAng-(1-7) with a single amino acid N-terminal extension stimulate ERK phosphorylation via the AT2 receptor. The interaction with the AT2 receptor of the N-terminally extended cAng-(1-7) depends on the amino acid at position at the very N-terminus "−1". At this N-terminal position "−1", denoted as $Xaa^1$ elsewhere, a positively or negatively charged amino acid or a hydrophobic amino acid led to high AT2 receptor specificity; a peptide extended with a hydrophilic amino acid without net charge such as Ser and Asn did not or hardly interact with the AT2 receptor. The thioether ring is required for the action of the N-extended cAng-(1-7) peptides via the AT2 receptor, since the AT2 antagonist PD123319 could not inhibit the Erk phosphorylation induced by a linear N-extended Ang-(1-7) analog.

Example 3. AT2 Receptor Stimulation is not Exerted by cAng-(1-7) Analogs with Two Amino Acids N-Terminal Extension Introduction.

In this example it is investigated whether or not cAng-(1-7) analogs with an N-terminal extension of two amino acids stimulate the AT2 receptor. As in Example 2, peptide-induced ERK phosphorylation in HBE cells was measured and the dependence of this phosphorylation on the AT2 antagonist PD123319.

Materials and Methods.

Thioether bridged peptide synthesis and cell culture and measurement of Erk1- and total Erk phosphorylation were essentially as in example 2.

Results.

FIG. 3A shows that both the thioether-bridged analog IcAng-(1-7) and DcAng-(1-7) induced Erk1 phosphorylation, which is inhibited by the pretreatment with PD 123319. However, in the case of a two-amino acid extension as in IDcAng-(1-7)—and in the case of the linear IDDRVAIHA (SEQ ID NO:6)-induced Erk phosphorylation, no inhibition at all by pretreatment with the AT2 antagonist PD123319 was obtained (FIG. 3B).

Conclusions.

Example 2 had already demonstrated that a ring was required for the AT2 receptor stimulation of N-extended Ang-(1-7). Consistently also the extension with two amino acids of a linear variant did not stimulate the AT2 receptor. Since the nonlinear cAng-(1-7) N-terminally extended with two amino acids did neither stimulate the AT2 receptor, it is concluded that one amino acid N-terminal extension of cAng-(1-7) is the N-terminal extension limit for AT2 receptor agonists.

Example 4. N-Extended cAng-(1-7) Analogs do not Act Via the Mas Receptor

Introduction.

In this example it is demonstrated that the Mas receptor antagonist D-Pro7-Ang-(1-7) can not inhibit the KcAng-(1-7) and YcAng-(1-7)-induced vasodilation in precontracted aorta rings from Sprague Dawley rats.

Materials and Methods.

D-Pro7-ang-(1-7), ang-(1-7) with a D-isomer of proline at position 7, which is a Mas-receptor antagonists, was from JPT and purified by HPLC prior to use. This antagonist was used as in Kluskens et al 2009: 10 min before addition of 30 nM PE at a concentration of 0.1 µM. Other materials and methods were as in example 1.

Results.

FIG. 4 demonstrates that the Mas receptor antagonist D-Pro7 does not inhibit the KcAng-(1-7) and YcAng-(1-7)-induced vasodilation in precontracted aorta rings from Sprague Dawley rats.

Conclusion.

KcAng-(1-7) and YcAng-(1-7) do not act via de Mas receptor.

The invention claimed is:

1. A method of treating a subject having a condition in which selective agonism of the angiotensin II type 2 (AT2) receptor is desired and/or required, comprising administering to the subject an effective amount of a cyclic peptide compound consisting of the amino acid sequence $Xaa^1$-Asp-Arg-Val-Abu/Ala-Ile-His-Abu/Ala comprising a thioether-bridge linkage between the side chains of Abu/Ala at position 5 and Abu/Ala at position 8, wherein $Xaa^1$ is selected from the group consisting of Lys, Tyr, Asp, Ile, Asn and Ser; wherein said condition is diabetes, myocardial infarction, renal hypertension, stroke, alopecia, an inflammatory lung disorder, fibrosis, or wherein said condition requires augmentation of erythropoiesis.

2. The method according to claim 1, wherein $Xaa^1$ is a D-stereoisomer.

3. The method according to claim 1, wherein $Xaa^1$ is Lys.

4. The method according to claim 1, wherein $Xaa^1$ is Tyr.

5. The method according to claim 1, wherein $Xaa^1$ is Asp.

6. The method according to claim 1, wherein $Xaa^1$ is Ile.

7. The method according to claim 1, wherein $Xaa^1$ is Asn.

8. The method according to claim 1, wherein $Xaa^1$ is Ser.

9. The method according to claim 1, wherein the amino acid at position 5 is a D-stereoisomer of Ala.

10. The method according to claim 1, wherein the amino acid at position 8 is an L-stereoisomer of Ala.

11. The method according to claim 1, wherein the amino acid at position 5 is a D-stereoisomer of Ala and the amino acid at position 8 is an L-stereoisomer of Ala.

12. The method according to claim 1, wherein the peptide compound consists of the amino acid sequence of Lys-Asp-Arg-Val-Abu/Ala-Ile-His-Abu/Ala (SEQ ID NO: 3) under the provision that the peptide does not contain two Abu (2-aminobutyric acid) residues.

13. The method according to claim 12, wherein Lys in the peptide compound is a D-stereoisomer.

14. The method according to claim 1, wherein the peptide compound consists of the amino acid sequence of Tyr-Asp-Arg-Val-Abu/Ala-Ile-His-Abu/Ala (SEQ ID NO: 5) under the provision that the peptide does not contain two Abu (2-aminobutyric acid) residues.

15. The method according to claim 1, wherein the peptide compound consists of the amino acid sequence of Asp-Asp-Arg-Val-Abu/Ala-Ile-His-Abu/Ala (SEQ ID NO: 4) under the provision that the peptide does not contain two Abu (2-aminobutyric acid) residues.

16. The method according to claim 1, wherein the peptide compound consists of the amino acid sequence of Ile-Asp-Arg-Val-Abu/Ala-Ile-His-Abu/Ala (SEQ ID NO: 6) under the provision that the peptide does not contain two Abu (2-aminobutyric acid) residues.

17. The method according to claim 1, wherein the peptide compound consists of the amino acid sequence of Asn-Asp-Arg-Val-Abu/Ala-Ile-His-Abu/Ala (SEQ ID NO: 7) under the provision that the peptide does not contain two Abu (2-aminobutyric acid) residues.

18. The method according to claim 1, wherein the peptide compound consists of the amino acid sequence of Ser-Asp-Arg-Val-Abu/Ala-Ile-His-Abu/Ala (SEQ ID NO: 15) under the provision that the peptide does not contain two Abu (2-aminobutyric acid) residues.

* * * * *

SEQUENCE LISTING

```
<160> NUMBER OF SEQ ID NOS: 15

<210> SEQ ID NO 1
<211> LENGTH: 8
<212> TYPE: PRT
<213> ORGANISM: Homo sapiens

<400> SEQUENCE: 1

Asp Arg Val Tyr Ile His Pro Phe
1               5

<210> SEQ ID NO 2
<211> LENGTH: 8
<212> TYPE: PRT
<213> ORGANISM: Artificial
<220> FEATURE:
<223> OTHER INFORMATION: cyclic AT2 receptor antagonist general formula
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: VARIANT
<222> LOCATION: (4)..(4)
<223> OTHER INFORMATION: May also be Val
```

```
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: THIOETH
<222> LOCATION: (5)..(8)
<220> FEATURE:
<221> NAME/KEY: VARIANT
<222> LOCATION: (6)..(6)
<223> OTHER INFORMATION: May also be Val
<220> FEATURE:
<221> NAME/KEY: MISC_FEATURE
<222> LOCATION: (8)..(8)
<223> OTHER INFORMATION: Xaa can be any naturally occurring amino acid

<400> SEQUENCE: 2

Xaa Asp Arg Ile Xaa Ile His Xaa
1               5

<210> SEQ ID NO 3
<211> LENGTH: 8
<212> TYPE: PRT
<213> ORGANISM: Artificial
<220> FEATURE:
<223> OTHER INFORMATION: cyclic AT2 receptor antagonist
<220> FEATURE:
<221> NAME/KEY: THIOETH
<222> LOCATION: (5)..(8)
<220> FEATURE:
<221> NAME/KEY: VARIANT
<222> LOCATION: (5)..(5)
<223> OTHER INFORMATION: May be Abu
<220> FEATURE:
<221> NAME/KEY: VARIANT
<222> LOCATION: (8)..(8)
<223> OTHER INFORMATION: May be Abu

<400> SEQUENCE: 3

Lys Asp Arg Val Ala Ile His Ala
1               5

<210> SEQ ID NO 4
<211> LENGTH: 8
<212> TYPE: PRT
<213> ORGANISM: Artificial
<220> FEATURE:
<223> OTHER INFORMATION: cyclic AT2 receptor antagonist
<220> FEATURE:
<221> NAME/KEY: THIOETH
<222> LOCATION: (5)..(8)
<220> FEATURE:
<221> NAME/KEY: VARIANT
<222> LOCATION: (5)..(5)
<223> OTHER INFORMATION: May be Abu
<220> FEATURE:
<221> NAME/KEY: VARIANT
<222> LOCATION: (8)..(8)
<223> OTHER INFORMATION: May be Abu

<400> SEQUENCE: 4

Asp Asp Arg Val Ala Ile His Ala
1               5

<210> SEQ ID NO 5
<211> LENGTH: 8
<212> TYPE: PRT
<213> ORGANISM: Artificial
<220> FEATURE:
<223> OTHER INFORMATION: cyclic AT2 receptor antagonist
```

```
<220> FEATURE:
<221> NAME/KEY: THIOETH
<222> LOCATION: (5)..(8)
<220> FEATURE:
<221> NAME/KEY: VARIANT
<222> LOCATION: (5)..(5)
<223> OTHER INFORMATION: May be Abu
<220> FEATURE:
<221> NAME/KEY: VARIANT
<222> LOCATION: (8)..(8)
<223> OTHER INFORMATION: May be Abu

<400> SEQUENCE: 5

Tyr Asp Arg Val Ala Ile His Ala
1               5

<210> SEQ ID NO 6
<211> LENGTH: 8
<212> TYPE: PRT
<213> ORGANISM: Artificial
<220> FEATURE:
<223> OTHER INFORMATION: cyclic AT2 receptor antagonist
<220> FEATURE:
<221> NAME/KEY: THIOETH
<222> LOCATION: (5)..(8)
<220> FEATURE:
<221> NAME/KEY: VARIANT
<222> LOCATION: (5)..(5)
<223> OTHER INFORMATION: May be Abu
<220> FEATURE:
<221> NAME/KEY: VARIANT
<222> LOCATION: (8)..(8)
<223> OTHER INFORMATION: May be Abu

<400> SEQUENCE: 6

Ile Asp Arg Val Ala Ile His Ala
1               5

<210> SEQ ID NO 7
<211> LENGTH: 8
<212> TYPE: PRT
<213> ORGANISM: Artificial
<220> FEATURE:
<223> OTHER INFORMATION: cyclic AT2 receptor antagonist
<220> FEATURE:
<221> NAME/KEY: THIOETH
<222> LOCATION: (5)..(8)
<220> FEATURE:
<221> NAME/KEY: VARIANT
<222> LOCATION: (5)..(5)
<223> OTHER INFORMATION: May be Abu
<220> FEATURE:
<221> NAME/KEY: VARIANT
<222> LOCATION: (8)..(8)
<223> OTHER INFORMATION: May be Abu

<400> SEQUENCE: 7

Asn Asp Arg Val Ala Ile His Ala
1               5

<210> SEQ ID NO 8
<211> LENGTH: 9
<212> TYPE: PRT
<213> ORGANISM: Artificial
<220> FEATURE:
<223> OTHER INFORMATION: control cyclic peptide

<400> SEQUENCE: 8

Ile Asp Asp Arg Val Ala Ile His Ala
1               5
```

```
<210> SEQ ID NO 9
<211> LENGTH: 8
<212> TYPE: PRT
<213> ORGANISM: Artificial
<220> FEATURE:
<223> OTHER INFORMATION: linear AT2 receptor antagonist

<400> SEQUENCE: 9

Lys Asp Arg Val Cys Ile His Cys
1               5

<210> SEQ ID NO 10
<211> LENGTH: 8
<212> TYPE: PRT
<213> ORGANISM: Artificial
<220> FEATURE:
<223> OTHER INFORMATION: linear AT2 receptor antagonist

<400> SEQUENCE: 10

Tyr Asp Arg Val Cys Ile His Cys
1               5

<210> SEQ ID NO 11
<211> LENGTH: 8
<212> TYPE: PRT
<213> ORGANISM: Artificial
<220> FEATURE:
<223> OTHER INFORMATION: linear AT2 receptor antagonist

<400> SEQUENCE: 11

Asp Asp Arg Val Cys Ile His Cys
1               5

<210> SEQ ID NO 12
<211> LENGTH: 8
<212> TYPE: PRT
<213> ORGANISM: Artificial
<220> FEATURE:
<223> OTHER INFORMATION: linear AT2 receptor antagonist

<400> SEQUENCE: 12

Ile Asp Arg Val Cys Ile His Cys
1               5

<210> SEQ ID NO 13
<211> LENGTH: 8
<212> TYPE: PRT
<213> ORGANISM: Artificial
<220> FEATURE:
<223> OTHER INFORMATION: linear AT2 receptor antagonist

<400> SEQUENCE: 13

Asn Asp Arg Val Cys Ile His Cys
1               5

<210> SEQ ID NO 14
<211> LENGTH: 8
<212> TYPE: PRT
<213> ORGANISM: Artificial
<220> FEATURE:
<223> OTHER INFORMATION: linear AT2 receptor antagonist

<400> SEQUENCE: 14

Ser Asp Arg Val Cys Ile His Cys
1               5
```

```
<210> SEQ ID NO 15
<211> LENGTH: 8
<212> TYPE: PRT
<213> ORGANISM: Artificial
<220> FEATURE:
<223> OTHER INFORMATION: cyclic AT2 receptor antagonist
<220> FEATURE:
<221> NAME/KEY: VARIANT
<222> LOCATION: (5)..(5)
<223> OTHER INFORMATION: May be Abu
<220> FEATURE:
<221> NAME/KEY: VARIANT
<222> LOCATION: (8)..(8)
<223> OTHER INFORMATION: May be Abu

<400> SEQUENCE: 15

Ser Asp Arg Val Ala Ile His Ala
1               5
```